United States Patent [19]

Seidehamel et al.

[11] 3,933,998
[45] Jan. 20, 1976

[54] 4-[2-(ISOPROPYLAMINO)ETHYL]-PYROCATECHOL INTRAOCULAR PRESSURE LOWERING PROCESS

[75] Inventors: Richard J. Seidehamel; Kendrick W. Dungan, both of Evansville, Ind.

[73] Assignee: Mead Johnson & Company, Evansville, Ind.

[22] Filed: Nov. 4, 1974

[21] Appl. No.: 520,388

[52] U.S. Cl. .................... 424/28; 424/78; 424/330
[51] Int. Cl.² ........................................ A61K 31/135
[58] Field of Search ............................. 424/330, 28

[56] References Cited
UNITED STATES PATENTS 3,849,577  11/1974  Holland ............................. 424/330

OTHER PUBLICATIONS

Luduena et al., Chemical Abstracts 64: 1188(f) (1966).
Luduena et al., Chemical Abstracts 64: 2591(a) (1966).
Weekers et al., Chemical Abstracts 66: 64226g (1967).
Fortenberry et al., Chemical Abstracts 71: 59474(b) (1969).
Leaders et al., Chemical Abstracts 74: 123505(d) (1971).
Podos et al., Chemical Abstracts 77: 14378(f) (1972).

*Primary Examiner*—Norman A. Drezin
*Attorney, Agent, or Firm*—Robert H. Uloth; Robert E. Carnahan

[57] ABSTRACT

Topical administration of 4-[2-(isopropylamino)ethyl]pyrocatechol to the mammalian eye reduces intraocular pressure without side effects generally associated with adrenergic activation such as tachycardia, mydriasis, hypertension and hypotension.

5 Claims, No Drawings

4-[2-(ISOPROPYLAMINO)ETHYL]PYROCATECHOL INTRAOCULAR PRESSURE LOWERING PROCESS

BACKGROUND OF THE INVENTION

This invention involves a process and compositions of the drug, bio-affecting, and body treating type. More specifically, this invention deals with a process for treatment of ocular hypertension by ocular instillation of 4-[2-(isopropylamino)ethyl]pyrocatechol.

Ocular hypertension is associated with glaucoma, a disease of the eye characterized by a progressive increase in intraocular pressure which occurs over a prolonged period of time which if untreated continues until the optic nerve is damaged and blindness results. The goal in the treatment of glaucoma is to reduce the intraocular pressure sufficiently to prevent damage to the optic nerve. The adrenergic amine epinephrine applied topically to the eye is a widely used treatment. Miotics which include certain parasympathomimetics such as pilocarpine and cholinesterase inhibitors such as physostigmine are also widely used topically. Improved drugs for topical application to the eye to reduce intraocular pressure are needed, however, due to side effects caused by existing drugs. Common undesired effects induced by the miotics include twitching of the eye lids, browache, headache, ocular pain, conjunctival congestion, etc. Localized allergy occasionally develops. Absorption of the topically applied drug occasionally causes systemic effects. This is particularly true with the cholinesterase inhibitors which may cause salivation, sweating, nausea, vomiting, bradycardia, hypotension, etc., and with adrenergic (sympathomimetic) agents which may cause tachycardia, hypertension, headaches, sweating, tremors, etc. The alpha-adrenergic stimulating action of epinephrine, for instance, frequently causes mydriasis and sometimes retinal maculopathy on prolonged usage.

Isoproterenol, an adrenergic agent whose action differs from epinephrine in that it is considered almost exclusively a beta-adrenergic stimulator, has been evaluated by Ross and Drance, Arch. Ophthal., 83, 39–43 (1970), in patients with ocular hypertension. Satisfactory reduction in intraocular pressure as a result of ocular instillation of a 5% isoproterenol hydrochloride solution was obtained but, concomitant side effects of a serious nature were also seen which prohibited the practical use of isoproterenol for glaucoma treatment. Among side effects associated with the administration of isoproterenol for reduction of intraocular pressure were marked and dangerous tachycardia of up to 100 to 150 beats per minute as well as palpitations, a nervous feeling, and weakness.

F. E. Leaders, et al., Arch. Int. Pharmacodyn., 183, 93–106 (1970), in reporting a study of the mydriatic and ocular hypotensive effects of selected phenethylamine derivatives, indicated that dopamine hydrochloride reduces intraocular pressure in the rabbit eye induced by topical application of 2.5% formalin according to the test method of B. Fortenberry, et al., Proc. Soc. Exp. Biol., New York, 131, 637 (1969).

SUMMARY OF THE INVENTION

This invention relates to a process for lowering intraocular pressure. More particularly, this invention is concerned with a process of lowering intraocular pressure in the mammalian eye which comprises topical application thereto of an effective ophthalmologically acceptable amount for lowering intraocular pressure of a compound selected from the group consisting of 4-[2-(isopropylamino)ethyl]pyrocatechol represented by the formula below

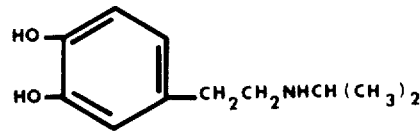

and ophthalmologically acceptable acid addition salts thereof.

Other aspects of this invention include pharmaceutical compositions for practicing the process for lowering intraocular pressure and methods of administration by polymeric insert or soft contact lens.

Topical administration of 4-[2-(isopropylamino)ethyl]pyrocatechol to the mammalian eye effectively lowers intraocular pressure without the concomitant appearance of any significant undesirable side effects such as increased pupil size and heart rate or effects on blood pressure.

In accord with the present invention, 4-[2-(isopropylamino)ethyl]pyrocatechol or an ophthalmologically acceptable salt thereof applied topically to the eye in an effective ophthalmologically acceptable amount provides a therapeutically useful reduction in intraocular pressure which has a duration of from 4 to 6 hours. It is to be understood that the term "effective ophthalmologically acceptable amount" as used herein refers to the quantity of active ingredient necessary to lower intraocular pressure without causing any significant toxic, harmful or deleterious effects such as irritation, pain, allergic reaction, mydriasis, or side effects associated with adrenergic activation following systemic absorption such as tachycardia, systemic hypertension and hypotension. The process of the present invention comprises topical administration of a composition comprised of 4-[2-(isopropylamino)ethyl]pyrocatechol or an ophthalmologically acceptable salt thereof containing an amount chemically equivalent to from 0.16% to 5.2% by weight of the base form of 4-[2-(isopropylamino)ethyl]pyrocatechol in an amount sufficient to deliver an effective dose equivalent to from 0.08 mg. to 10.4 mg. of said base to each eye and a non-toxic pharmaceutically acceptable ophthalmological carrier therefor. The term "non-toxic" as used herein defines a substance which exhibits substantially no toxicity when administered in the process of the present invention.

When 4-[2-(isopropylamino)ethyl]pyrocatechol is administered topically to the mammalian eye, a solution having a concentration in the range of 0.16% to 5.2% by weight and preferably 0.16% to 3.4% by weight, the latter in an aqueous isotonic vehicle such as 0.9% sodium chloride, is preferred. One to four drops of such solution is sufficient. Other vehicles and additional active ingredients may be included in the compositions.

The term "ophthalmologically acceptable acid addition salts" used herein in describing the salts of the phenethanolamines characterized by Formula I is intended to define those salts and compositions which are substantially non-toxic or non-irritating on topical application to the eye and otherwise generally in accord with the requirements, practicalities and good pharmaceutical practice with respect to ophthalmic products. By way of example there can be mentioned those salts derived from organic or inorganic acids which are not irritating to the eye such as hydrochloric, hydrobromic, sulfuric, phosphoric, methanesulfonic, acetic, citric, malic, succinic, lactic, tartaric, benzoic, and the like.

In practicing the process of the present invention, ophthalmologically acceptable water soluble salts of 4-[2-(isopropylamino)ethyl]pyrocatechol such as the tartrate, bitartrate, sulfate or hydrochloride are preferred. For purposes of this disclosure, the weight concentrations of the solutions employed in the process of the invention are expressed herein in terms of the base form of 4-[2-(isopropylamino)ethyl]pyrocatechol.

This invention is further illustrated by the following specific examples given below which are not intended to be limiting in any manner.

DESCRIPTION OF SPECIFIC EMBODIMENTS

Example 1

INTRAOCULAR PRESSURE REDUCTION BY OCULAR INSTILLATION OF 4-[2-(ISOPROPYLAMINO)ETHYL]PYROCATECHOL

To aid in the diagnosis of primary open angle glaucoma in man, a so-called water provocative test is used. According to the diagnostic procedure the patient is required to drink a predetermined quantity of water and the intraocular pressure is measured at intervals thereafter. This procedure has been adapted to the evaluation of chemical entities possessing anti-glaucoma activity in rabbits by McDonald, et al., Archives of Ophthalmology, 82, 381–384 (1969), and validated with respect to various drugs which are effective for lowering intraocular pressure in man including epinephrine bitartrate, 1-isoproterenol bitartrate, pilocarpine hydrochloride, physostigmine salicylate, etc. The McDonald, et al. (supra) "Water-Loading" test model for evaluating drugs with potential anti-glaucoma activity eliminates many of the disadvantages incurred with other experimental ocular hypertension models. For instance, it does not intail application of irritating compounds such as formalin employed in the test method of B. Fortenberry, et al. (supra) which may alter drug penetration to an unknown extent. The irritation induced formalin ocular hypertension test method presumably based on "inflammation and edema" is not as satisfactory in assessing anti-glaucoma activity as the "Water-Loading" test of McDonald, et al. which is similar to that of the clinically established water-provocative test for primary open-angle glaucoma.

Operativeness of the present invention according to adaptation of the McDonald, et al. "Water-Loading test" is demonstrated as follows. Female New Zealand white rabbits weighing from 1.8 to 2.5 kg. each were grossly examined for ocular defects that might preclude their use in the test. Each rabbit was kept unanesthetized in a restrainer box throughout the experiment. Food was withheld for approximately 18 hours prior to the use of the animals in the experiment. Intraocular pressures were measured with a MacKay-Marg Model No. 12 electronic tonometer (Biotronics, Inc., 838 Butte Street, Redding, Calif. 96001; E. Marg, Journal of the American Optometric Association, 34, 961–5 (1963)).

Intraocular pressure was measured at the outset to obtain a normal value and then the rabbits were given tap water, approximately 60 ml./kg. of body weight rapidly via gavage. Intraocular pressures were again measured 10, 20 and 30 minutes later to determine the peak increase in intraocular pressure resulting from the water loading. The procedure was then repeated in the same animals 2 hours following topical application of the test drug (e.g., 4-[2-(isopropylamino)ethyl]-pyrocatechol) or control solutions. In each instance, after water load, there is a substantial increase in intraocular pressure (unless controlled by the test drug) which reaches maximal elevation within 30 minutes and returns to pretreatment levels before the next water load.

Drug solutions were prepared by dissolving the test agent in 0.9% aqueous saline vehicle. In the test procedure, 100 $\mu$l. (approximately two drops) of the test solution was applied to one eye and 0.9% saline was applied to the contralateral eye which serves as the control eye during the course of the experiment. Pretreatment measurements (designated 0 hours) were previously made of normal intraocular pressure, and of the response to water loading to establish that no significant difference in intraocular pressure between the test eye and the contralateral control eye existed prior to the administration of the solution of the test agent. Test solutions were randomized between right and left eyes. By comparing the change (reduction) in intraocular pressure in the test eye compared to the contralateral eye, which serves as a control, a measure of the effectiveness of the test agent as an intraocular pressure lowering agent is obtained. The diameter of the pupil was measured under constant illumination to the nearest 0.5 millimeter with a clear straight edge ruler. Blood pressure and heart rate were measured in unanesthetized rabbits with a force displacement transducer via cannulation of the central artery of the xylocaine infiltrated ear. Separate groups of animals were used for the cardiovascular and intraocular pressure experiments.

The data presented in Table I indicates the intraocular lowering effect of 4-[2-(isopropylamino)ethyl]-pyrocatechol compared to that obtained with dl-isoproterenol, a clinically evaluated intraocular lowering agent (refer to Ross and Drance, supra), and dopamine.

TABLE I

COMPARATIVE EFFECTS OF 4-[2-(ISOPROPYLAMINO)ETHYL]PYROCATECHOL, dl-ISOPROTERENOL AND DOPAMINE ON INTRAOCULAR PRESSURE TWO HOURS AFTER TOPICAL APPLICATION TO EYES OF UNANESTHETIZED RABBITS

| | | Intraocular Pressure[a] (mean ± S.E.) | | | | | |
|---|---|---|---|---|---|---|---|
| | | Pretreatment mm Hg. | | Post-Treatment[b] mm Hg. | | Reduction[c] | |
| Drug | Conc. Tested % | Drug Eyes | Saline Eyes | Drug Eyes | Saline Eyes | mm Hg | % |
| 4-[2-(Isopropyl-amino)ethyl]-pyrocatechol HCl | 2.8[d] | 28.3 ± 2.0 | 29.5 ± 1.5 | 22.7 ± 0.7 | 31.8 ± 1.3 | 9.2 ± 1.1 | 28.5 ± 2.4 |
| dl-Isoproterenol HCl | 3.0[d] | 29.8 ± 2.0 | 31.2 ± 2.0 | 25.7 ± 1.6 | 30.2 ± 2.0 | 4.5 ± 1.3 | 14.4 ± 3.7 |
| Dopamine HCl | 2.3[d] | 32.4 ± 0.9 | 31.6 ± 0.8 | 34.8 ± 1.2 | 34.4 ± 1.2 | 0 | 0 |
| Dopamine HCl | 4.0[e] | 29.4 ± 0.8 | 29.4 ± 0.8 | 34.4 ± 0.7 | 33.6 ± 1.2 | 0 | 0 |

[a]Water load elevated intraocular pressure in rabbits (5 or 6 animals).
[b]Two hours after topical drug application to the eye.
[c]Reduction of intraocular pressure in drug-treated as compared to contralateral, saline-treated eyes.
[d]Drug concentrations are equimolar with respect to base.
[e]Concentration employed by F. E. Leaders, et al. (supra) in formalin induced ocular hypertension test.

TABLE II

COMPARATIVE EFFECTS OF EQUIMOLAR INTRAOCULAR PRESSURE LOWERING AMOUNTS of 4-[2-(ISOPROPYLAMINO)ETHYL]PYROCATECHOL, AND dl-ISOPROTERENOL ON HEART RATE TWO HOURS AFTER TOPICAL APPLICATION TO EYES OF UNANESTHETIZED RABBITS

| | | | Heart Rate (mean ± S. E.) Post-Treatment[a] | | |
|---|---|---|---|---|---|
| Drug | No. Animals | Pretreatment Beats/min | Beats/min | Increase[b] Beats/min | % |
| 4-[2-(Iso-propylamino)-ethyl]pyro-catechol HCl | 3 | 221.7 ± 10.9 | 233.0 ± 14.5 | 11.7 ± 7.3 | 5.2 ± 3.1 |
| dl-Isoproter-enol HCl | 4 | 233.0 ± 24.8 | 371.8 ± 10.1 | 138.8 ± 20.9 | 65.6 ± 19.2 |
| Saline | 8 | 216.5 ± 11.5 | 243.1 ± 11.2 | 27.9 ± 7.9 | 14.0 ± 4.5 |

[a]Maximum occurring within 60 minute interval after topical drug application to the eye.
[b]Post-treatment as compared to pretreatment heart rate.

Pretreatment values listed in Table I for intraocular pressure with respect to the drug eye and saline eye established that no initial significant difference existed prior to the administration of the test drug and therefore reduction in intraocular pressure is a valid measure of the effectiveness of the test agent.

The results set forth in Table I clearly establish that 4-[2-(isopropylamino)ethyl]pyrocatechol substantially reduces intraocular pressure whereas the homologous phenethylamine "dopamine" is completely inactive. As is evident from the data presented in Table II, the dose 4-[2-(isopropylamino)ethyl]pyrocatechol providing reduction in intraocular pressure has no significant effect on the heart rate while dl-isoproterenol produces a marked increase in heart rate. As to the slight increase in heart rate seen for 4-[2-(isopropylamino)ethyl]pyrocatechol this is not significant inasmuch as the saline solution which serves as a vehicle for administering the compound produces a 14% increase in heart rate as shown in Table II.

Example 2

Pharmaceutical Compositions Containing 4-[2-(Isopropylamino)Ethyl]Pyrocatechol

Pharmaceutical compositions comprised of 4-[2-(isopropylamino)ethyl]pyrocatechol and a non-toxic pharmaceutically acceptable ophthalmological carrier therefor which are suitable for ocular instillation are preferred for practice of the present invention. These include ophthalmic solutions and ointments. Aqueous ophthalmic solutions formulated in accord with good pharmaceutical practice as set forth for instance in Chapter 83 of Remington's Pharmaceutical Sciences, 14th Edition, Mack Publishing Company are preferred, although petrolatum based ointments may be employed. The ophthalmic solutions are sterile and preferably contain a bacteriological preservative to maintain sterility during use. The quaternary ammonium bacteriostats such as benzalkonium chloride are satisfactory. An antioxidant can also be employed if desired but in view of the fact that 4-[2-(isopropylamino)ethyl]pyrocatechol is much less susceptible to oxidative decomposition than phenethanolamine intraocular lowering agents such as isoproterenol and epinephrine it is generally not required. By way of example, suitable antioxidants include sodium bisulfite, N-acetylcysteine salts, sodium ascorbate and other water soluble ophthalmologically acceptable antioxidants known to the pharmaceutical art.

Ophthalmic solutions of 4-[2-(isopropylamino)ethyl]pyrocatechol may be adjusted with inert ingredients such as sodium chloride or boric acid to provide a solution which is comfortable for application to the eye. For example, compositions containing up to about 5.2% of 4-[2-(isopropylamino)ethyl]pyrocatechol with 0.9% sodium chloride, or an isotonically equivalent vehicle such as 1.9% boric acid are satisfactory.

Ointments are prepared with conventional petrolatum vehicles employing liquid petrolatum and white petrolatum in such proportions as to afford an ointment of desirable fluidity.

| Ophthalmic Solution | |
| --- | --- |
| 4-[2-(isopropylamino)-ethyl]pyrocatechol Hydrochloride | 3.50 g. |
| Benzalkonium chloride | 0.01 g. |
| Sodium bisulfite | 0.10 g. |
| Water, q.s. | 100.00 g. |

If desired, 0.9% by weight aqueous sodium chloride may replace water as the solvent. The solution is sterilized by filtration and asceptically packaged.

| Ophthalmic Ointment | |
| --- | --- |
| 4-[2-(isopropylamino)-ethyl]pyrocatechol, micronized | 1.1 g. |
| White petrolatum, q.s., Liquid petrolatum, q.s., | 100.0 g. |

The product is prepared and packaged under asceptic conditions to yield a sterile ointment.

4-[2-(Isopropylamino)ethyl]pyrocatechol and ophthalmologically acceptable acid addition salts thereof may also be applied to the eye through the vehicle of a polymeric insert or soft contact lens. For the latter purpose, the polymeric hydrophilic hydrogels prepared from polymers of acrylic and methacrylic esters, modified collagens, cross-linked polyether gels, cross-linked polyvinyl alcohol, or cross-linked partially hydrolyzed polyvinylacetate as disclosed in U.S. Pat. Nos. 2,976,576, 3,220,960, and 3,419,006 may be employed. Ocular inserts prepared from these or other polymeric materials which are insoluble in tear liquid but which may absorb tear liquid to form a swollen hydrogel as disclosed in U.S. Pat. Nos. 3,416,350 and 3,618,604 may also be employed. All such means of applying 4-[2-(isopropylamino)ethyl]pyrocatechol or an ophthalmologically acceptable salt thereof are included within the present invention as are compositions adapted for such use.

In practicing the process of the present invention for lowering intraocular pressure by topical administration of 4-[2-(isopropylamino)ethyl]pyrocatechol, an ophthalmologically acceptable polymeric ocular insert placed and retained in contact with an eyeball is preferred wherein the compound diffuses from the insert at a rate sufficient to provide an effective intraocular pressure lowering dose from 0.08 to 10.4 mg. over a period of 6 hours.

Ocular inserts particularly preferred in the practice of the process of the present invention are conventionally prepared, for example, by soaking the polymeric insert or soft lens in a 0.16% to 5.2% solution of 4-[2-(isopropylamino)ethyl]pyrocatechol or an ophthalmological salt thereof until equilibrium is established, which is generally within a period of 1 to 5 minutes. Inserts prepared in this manner diffuse at a rate sufficient to provide a dose of from 0.08 mg. to 10.4 mg. to the eyeball over a period of 6 hours.

What is claimed is:

1. A process for lowering elevated intraocular pressure in a patient suffering from primary open angle glaucoma comprising topically applying to said patient's eyes an effective ophtalmologically acceptable amount for lowering intraocular pressure of a compound selected from the group consisting of 4-[2-(isopropylamino)ethyl]pyrocatechol and ophthalmologically acceptable acid addition salts thereof.

2. The process of claim 1 wherein the ophthalmologically acceptable salt is water soluble and is applied topically in an aqueous solution wherein said solution contains a molar amount of said water soluble ophthalmologically acceptable salt equivalent to from 0.16 to 5.2% by weight of 4-[2-(isopropylamino)ethyl]pyrocatechol.

3. The process of claim 1 wherein the compound is 4-[2-(isopropylamino)ethyl]pyrocatechol.

4. The process of claim 1 wherein the compound is 4-[2-(isopropylamino)ethyl]pyrocatechol hydrochloride.

5. The process of claim 1 wherein said compound is topically applied by an ophthalmologically acceptable polymeric ocular insert placed and retained in contact with the eyeball, said compound being diffusible from said insert at a rate sufficient to provide an ophthalmologically acceptable effective intraocular pressure lowering dose thereof to the eyeball when said insert is in contact therewith.

* * * * *